United States Patent [19]

Hirose

[11] Patent Number: 4,931,968

[45] Date of Patent: Jun. 5, 1990

[54] DATA CORRECTION CIRCUIT FOR POSITION EMISSION COMPUTED TOMOGRAPH

[75] Inventor: Yoshiharu Hirose, Kyoto, Japan

[73] Assignee: Shimadzu Corporation, Kyoto, Japan

[21] Appl. No.: 199,839

[22] Filed: May 27, 1988

[30] Foreign Application Priority Data

May 30, 1987 [JP] Japan ................................. 62-137216

[51] Int. Cl.⁵ ........................ G06F 15/74; G06F 15/42
[52] U.S. Cl. ......................... 364/571.02; 364/571.01;
364/413.15; 364/413.13
[58] Field of Search ....................... 364/571.01, 571.02,
364/571.04, 413.13, 413.15; 250/363.02, 363.03,
363.04; 378/4, 162, 165

[56] References Cited

U.S. PATENT DOCUMENTS

| 4,473,749 | 9/1984 | Derenzo et al. | 250/363.04 |
| 4,511,980 | 4/1985 | Watanabe | 364/571.01 |
| 4,523,091 | 6/1985 | Persyk | 250/363.02 |
| 4,575,868 | 3/1986 | Ueda et al. | 250/363.03 |

*Primary Examiner*—Parshotam S. Lall
*Assistant Examiner*—V. Trans
*Attorney, Agent, or Firm*—Griffin, Branigan & Butler

[57] ABSTRACT

A data correction circuit having arithmetic units installed in a data bus for the purpose of carrying out corrections such as dead-time correction and decay correction. The data correction circuit also includes an address modification storage installed in an address bus for the purpose of changing raw data into a sinogram. As the size of memory matrices for positron ECT grows larger in recent years, software dependent on a CPU is apt to require more time for data processing and prevent image formation from taking place in real-time. The aim of the present invention is to allow data reduction and correction to be carried out in real-time.

7 Claims, 3 Drawing Sheets

DATA CORRECTION CIRCUIT FOR POSITION EMISSION COMPUTED TOMOGRAPH

BACKGROUND OF THE INVENTION

The present invention is of use in the field of imaging devices for use in medical diagnosis as well as in the field of digital data acquisition.

The present invention relates to a data acquisition circuit, and more particularly to a data correction circuit for use in positron ECT.

A positron emitted from a positron emitter combines with an electron and is annihilated. The results is that two gamma rays, each of which acquires 0.511 MeV of energy, are discharged in directions nearly making an angle of 180° with each other.

In positron ECT, therefore, two gamma rays detected at a time are regarded as indicative of a positron emitted and annihilated. For the purpose of such detection, it is most common to connect a coincidence circuit to each pair of detectors which face to each other. Every time a coincidence circuit is actuated, an additional 1 which indicates that an event has occurred is written into a particular location in a memory allotted to the pair of detectors connected to the actuated coincidence circuit. Consequently, the readout from this particular location after the end of the data acquisition process indicates the number of positrons emitted and annihilated along the line extending from one of the abovementioned pair of detectors to the other.

FIG. 3-(1) shows the construction of an ordinary memory matrix used in the above-described data acquisition. This memory matrix has an address capability of the number of detectors falling under one set multiplied by the number of detectors falling under the other set. In FIG. 3-(1), the ordinates denote the numbers i given to the detectors falling under one set, and the abscissas denote the numbers j given to the detectors falling under the other set.

A point (i,j) in this orthogonal coordinate system indicates that one of two gamma rays, which have been discharged as a result of the annihilation of a positron, has been incident on a detector i falling under one set, while the other of the two gamma rays has been incidendt on a detector j falling under the other set. Because (i,j) and (j,i) indecate one and the same pair of detectors, the accumulation of data occurs only in the region provided with oblique lines in FIG. 3-(1).

It is most common to reconstruct the image by convolution and back projection. Data to be subjected to these algorithms, i.e., a plurality of points (i,j) in FIG. 3-(1), are collected in a straight direction, and this direction is everchanging. These data have to be rearranged for the reconstruction of the image so that an angle $\theta$ (FIG. 4) made with the positive direction of a reference axis by a line perpendicular to the above-mentioned straight direction may be plotted on an ordinate against the distance of the straight direction from the origin of the reference axis on an abscissa. The data plotted in this manner are called sinogram, which is shown in FIG. 3-(2). These data are subjected to convolution by means of a reconstruction filter and then to back projection so as to be reconstructed in to a tomographic image.

So far, high resolution has been attained by increasing the number of detectors, with the result that the address capability of a memory matrix has been enlarged from 64×64 to 128×128, then to 256×256, and then to 512×512. Consequently, more time has come to be required for the above-described processing from raw data to a sinogram, and the final image formation is apt to be prevented from taking place in real-time.

Especially when an object to be imaged is in motion, dead-time correction has to be carried out on the basis of mean values, by which a large error is introduced. This holds true for the decay correction as well.

Another troubles is that the conventional positron ECT requires software for allowing the processing to proceed from raw data shown in FIG. 3-(1) to a sinogram shown in FIG. 3-(2).

SUMMARY OF THE INVENTION

In view of the above-described troubles involved in the conventional positron ECT, it is an object of the present invention to provide a data correction circuit for use in positron ECT, this data correction circuit being characterized in that hardware rather than software is utilized to utilize the data in the above-described manner and that this hardware includes arithmetic units so that operation efficiency per unit time may be improved to such an extent that dead-time corrections and decay correction can be carried out nearly in real-time.

The above-described object of the present invention is accomplished by providing a data correction circuit which comprises temporary storages for temporarily storing data outputted from coincidence circuits, a buffer storage capable of accommodating a plurality of frame data, an address modification storage installed in an address bus connecting the temporary storages to the buffer storage, an adder installed in the address bus and adapted to specify a base address given to each frame region provided in the buffer storage, and arithmetic units installed in a data bus connecting the temporary storages to the buffer storage carring out corrections such as dead-time correction and decay correction and for subjecting the data to operating together with a constant.

A preferred embodiment of the present invention is hereinafter described with reference to the accompanying drawings.

DESCRIPTION OF A PREFERRED EMBODIMENT

Figure 1:
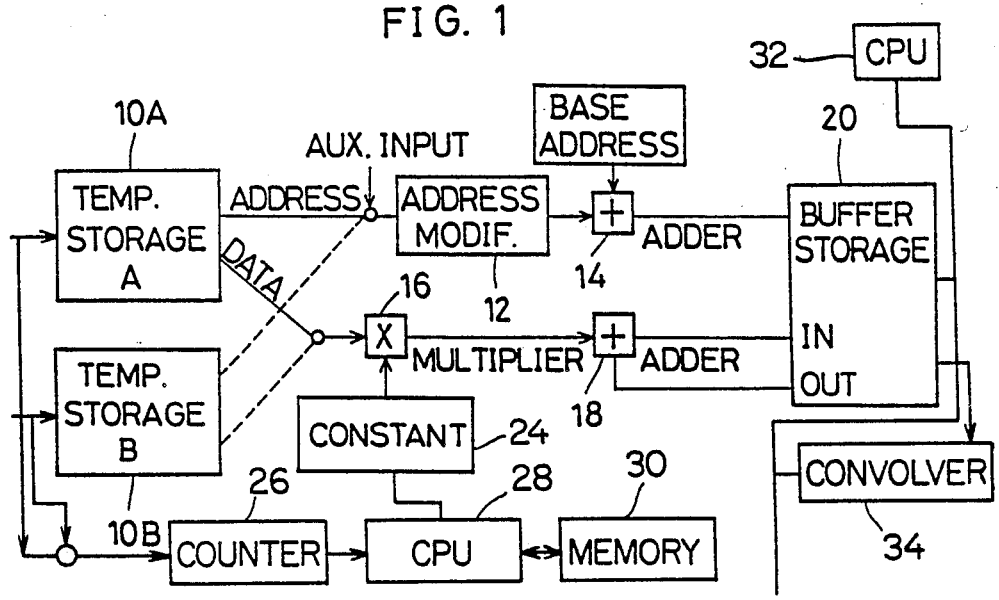
FIG. 1 is a schematic block diagram of an embodiment of the present invention.

An embodiment of the present invention shown in FIG. 1 includes temporary storages 10 connected to a coincidence circuit (not shown), an address modification storage 12 installed in an address bus and adapted to carry out the process of changing raw data into a sinogram, an adder 14 for the base address of each frame region, a multiplier 16 for multiplying each data by a coefficient which can be changed with time, an adder 18 for adding a new data to a preceding data, and a buffer storage 20 having a plurity of frame regions. Preferably, quickacting SRAMs are used as the temporary storages 10, and a large-capacity DRAM is used as the buffer storage 20. It will be understood that data, corrected and processed as subsequently described, may be fed to conventional image reconstruction circuits for convolution and back projection so as to reconstruct a tomographic image. Thus, the output from buffer storage 20 may be applied to a convolver 34 under control of a CPU 32.

Each data is stored forst in the temporary storage 10A and transmitted to the buffer storage 20 every 0.5 to 2 seconds. On its way to the buffer storage 20, the data is transferred to the temporary storage 10B and stored therin.

The transmission takes place substantially at the rate of a word per microsecond. Addresses given to the data in the temporary storages 10 are modified and permuted in the storage 12. The data per se are subjected to operations together with a constant (a coefficient), stored in a constant register 24, then fed to the buffer storage 20, and added to the preceding data so that data stored in the buffer storage 20 may be renewed.

The buffer storage 20 has a capacity of 1 MW or more, and is capable of arbitrary switchover from the base address of one frame region to the base address of another frame region so that a data may be stored in any memory location in the buffer storage 20.

Reference is now specifically made to the decay correction. In positron ECT, it is desirable to use a radioisotope (RI) having a longer half-life, because such an RI permits even its metabolites to be traced in the tissues. However, a given amount of an RI is reduced to one-half by radioactive decay when the half-life has elasped. Therefore, data collected after the lapse of the half-life do not give a clue to the distribution of the RI in vivo unless these data are multiplied by 2. In fact, decay correction is carried out by allowing the data to be multiplied by $$e^{\frac{0.693}{T}t}$$

at extremely short intervals of time, where t=half-life, and t=time which has elasped after start of data acquisition. This multipler is derived from the therorem that the number of atoms of the original radionuclide remaining after time t is given by $$N(t) = N(o)e^{-\frac{0.693}{T}t}$$

where
N(t)=number remaining
N(o)=original number.

Reference is now specifically made to the dead-time correction. It is a frequent occurrence that counting dead time cannot be given by a simple equation but can be found only from a calibration curve such as the one shown in FIG. 5. For the preparation of such a calibration curve, an RI is allowed to mix at various concentrations with water in a water tank, and this water is scanned. The counting rate is plotted on an ordinate against the concentration of the RI on an abscissa. Ideally, i.e., if an electronic circuit is free from counting loss, the counting rate is in a direct proportion to the concentration of the RI as shown by a line OA in FIG. 5. Actually, however, it is no exaggeration to say that no electronic circuits are free from counting loss, and the relationship between the counting rate and the concentration of the RI is represented by a curve OB in FIG. 5. Let it be supposed that a counting rate measured at a given concentration of the RI can be represented by a point C which lies on the curve OB. Then the line segment CC' represents an amount by which the counting rate should be corrected.

Figure 6:
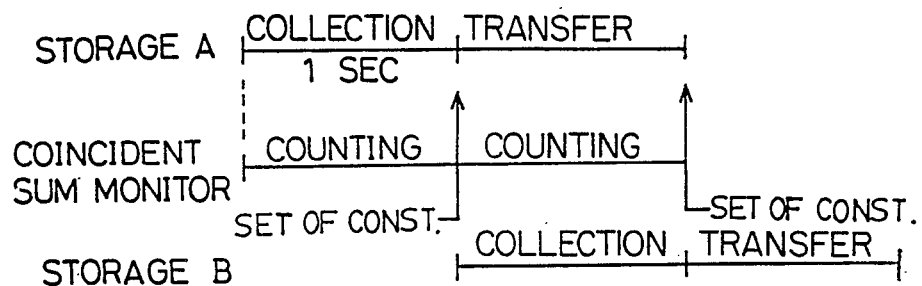
FIG. 6 is a drawing to help explain the process of dead-time correction to be carried out in accordance with the present invention.

FIG. 6 is a drawing to help explain the process of dead-time correction to be carried out in accordance with the present invention. Outputs taken from respective coincidence circuits (not shown) are summed up, and the sum total of these outputs are stored in a counter 26 (FIG. 1). Let it be supposed that data are taken out of this counter every one second. Then a difference between the data taken out at a given moment and the data taken out at the preceding moment represents the number of events which have occurred during the past one second. In other words, this difference corresponds to the concentration of the RI mentioned in the preceding paragraph as a criterion for determining the amount by which the counting rate should be corrected. This difference is set in the temporary storages 10 as a constant which changes every one second, in case of the above-mentioned supposition, so as to allow the dead-time correction to be carried out nearly in real-time. Actually, however, the temporary storage 10A has a capacity of as large as 256 kW. The implication is that 0.256 second is enough to transmit each data even if the transmission takes place at the rate of a word per microsecond. Therefore, one can draw nearer to real-time if the concentration of the RI is monitored at intervals of 0.256 second, i.e., under the condition of synchronism with the transfer of data.

Figure 5:
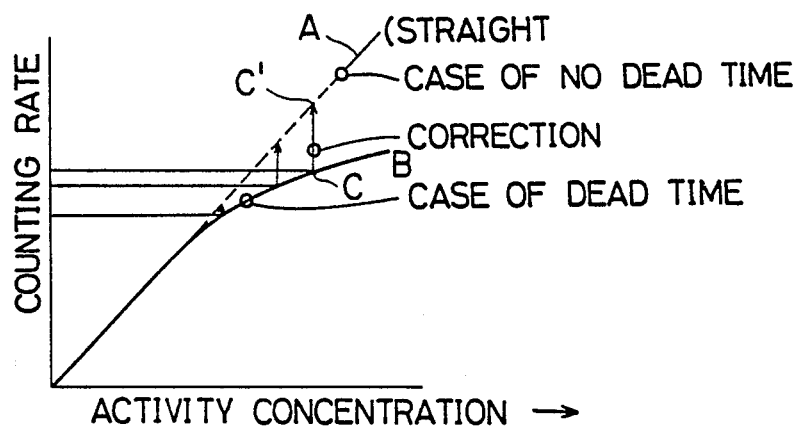
FIG. 5 is a graphical representation of a calibration curve, illustrating how an amount for dead-time correction is determined.

The constant to be set in the temporary storages 10 is the product of two amounts determined for decay correction and dead-time correction respectively, i.e., $$e^{\frac{0.693}{T}t}$$

and the amount represented by the line segment CC' in FIG. 5. It may be obtained from a memory 30 associated with a CPU 28 in response to the difference in counts obtained from counter 26, and applied to the constant register 24.

Alternatively, a parameter or parameters other than the above-mentioned two amounts may be used as a constant to be set in the temporary storages 10. For example, a data is multiplied by a constant $\alpha$, allowed to have a base address of 0, and transmitted to the buffer storage 20. Then the same data is multiplied by a constant $\beta$, allowed to have a base address of 2,000,000, and transmitted to the buffer storage 20. The result is that two differently weighted data are made from one data. Adding these two data to each other is tantamount to convolution. Consequently, the time which would otherwise be required for convolution can be done without. An arithmetic unit 22 shown in FIG. 2, which will be described later, is the very device for serving such a time-saving purpose.

The address modification storage 12 functions also as a means for picking out necessary data from among the whole of data supplied, or as a means for suppressing the data.

For dynamic framing, it is preferable to make a switchover from the base address of one frame region to the base address of another frame region every time a data is transmitted.

Figure 2:
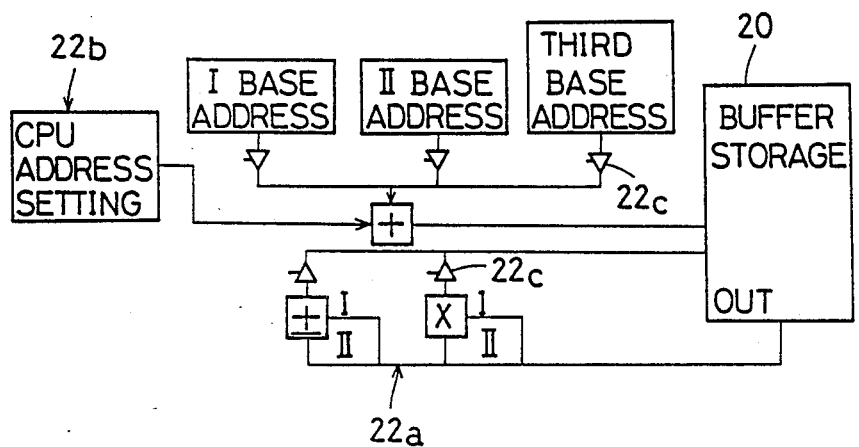
FIG. 2 illustrates a buffer storage and a circuit for image-to-image interpolation and arithmetic processing.
Figure 3:
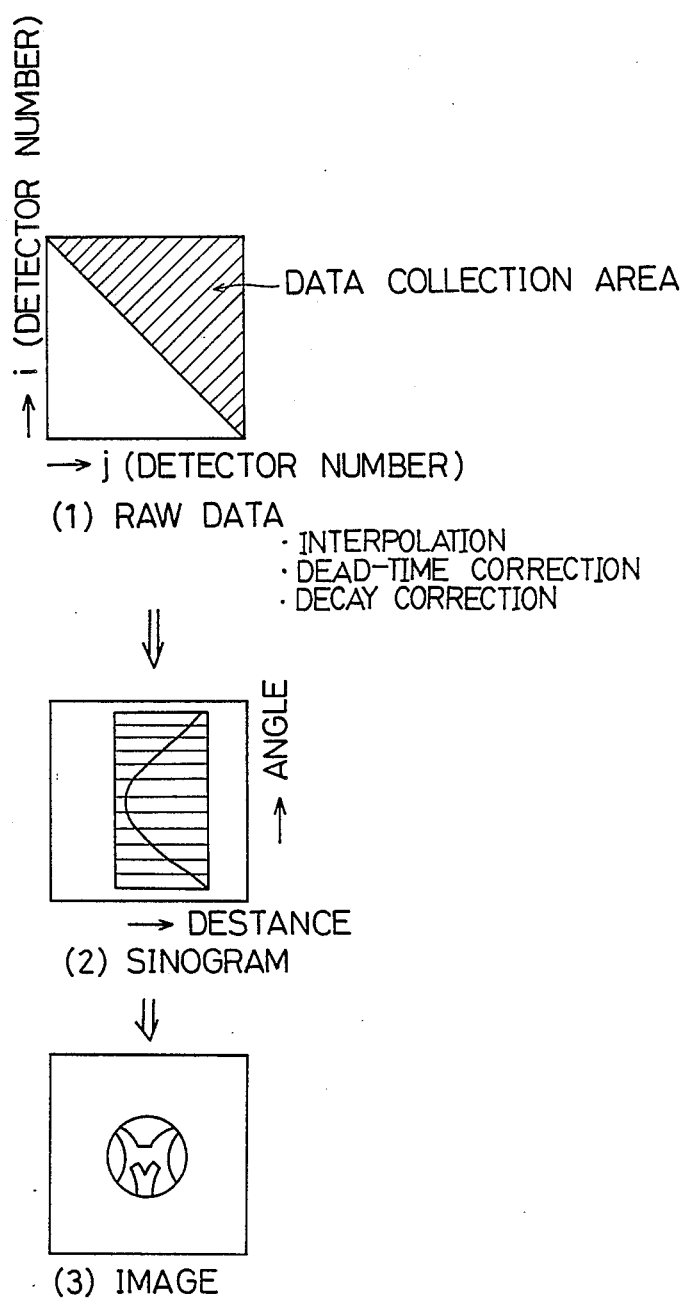
FIG. 3 is a schematic illustration to help explain the process with which a prior art ECT proceeds.
Figure 4:
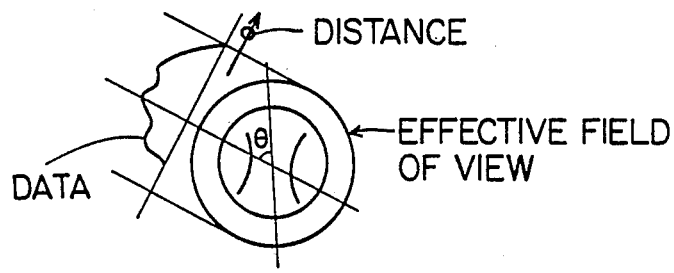
FIG. 4 is a drawing to help explain the principle of tomographic scanning.

Interpolating operations are performed by an arithmetic unit 22, which is attached to the buffer storage 20 as shown in FIG. 2. In an arithmetic unit 22a, a data stored in the buffer storage 20 provided with a first base address can be added to, subtracted from, or multiplied by a data provided with a second base address so that a data provided with a third base address may be obtained from such addition, subtraction or multiplication. Such operations can be combined with each other. For example, a plurality of frames can be added to each other, or a constant can be subtracted from each of them, or each of them can be multiplied by a constant so that they may be normalized, or one of them can be masked by another. These operations can be performed without the aid of a CPU. Consequently, operation efficiency per unit time can be improved. A device 22b for setting the addresses and gates 22c are controlled by a CPU.

In the case where the data correction circuit in accordance with the present invention is used in electrocardiogram (ECG) gated ECT, (the ECT input is gated by a signal from an ECG), an address taken from a coincidence circuit (not shown) is fed to an auxiliary input terminal shown in FIG. 1 and the multiplier 16 is allowed to receive a constant of 1 from the constant register 24. Then, ordinary data acquisition can be carried out, wherein the count is increased by one every time an event occurs in a modified address in the buffer storage 20. Data divided into n parts can be collected in the buffer storage 20 if a switchover from the base address of one frame region to the base address of another frame region is made at the rate of one nth of the period of the R—R wave, where n=2 to 32.

Although processing such as dead-time correction and decay correction can be carried out without the aid of a CPU, the CPU 28 may be used for the time sequencing of the operation of the arithmetic units installed in the address bus and the data bus. In some instances, the functions of CPUs 32 and 28 may be performed by a single CPU.

The temporary storages 10 may be monitored so that a constant or a coefficient may be set in the multiplier 16 every time a new data is fed to the temporary storages 10. A means for such monitoring may be provided as a function of the CPU.

Thus the present invention has an effect of making the data throughput higher so as to meet a demand for higher resolution and dynamic positron ECT studies. Processing such as dead-time correction and decay correction can be carried out nearly in real-time. The present invention has another effect of improving the quantitative properties of measurement in positron ECT, and can be used for data acquisition in ECG gated ECT as well.

What is claimed is:

1. A data correction circuit for use in a positron ECT wherein uncorrected data is produced by coincidence circuits upon annihilation of positrons, said data correction circuit comprising:

first and second temporary storages for temporarily storing uncorrected data produced by the coincidence circuits, one of said temporary storages collecting data while the other outputs uncorrected data;

a buffer storage for storing data in a plurality of addressable frame regions;

a data circuit and an address circuit connected between said temporary storages and said buffer storage;

an address modification storage connected in said address circuit;

an adder responsive to said address modification storage and a source of region base addresses for addressing said buffer storage;

means for storing a constant; and arithmetic means connecting in said data circuit for performing dead time correction and decay correction on said data by performing arithmetic operations on uncorrected data from said temporary storages, said arithmetic means being connected to said means for storing a constant and including means resposive to said means for storing a constant for modifying said uncorrected data according to said constant.

2. A data correction circuit as claimed in claim 1 and further comprising circuit means responsive to said buffer storage for interpolating and arithmetically processing corrected data in said buffer storage, and image reconstruction means connected to said buffer storage for processing data said buffer storage for image reconstruction, data in said buffer storage being transmitted to said image reconstruction means and said circuit means each time data is transmitted from said temporary storages to said buffer storage.

3. A data correction circuit as claimed in claim 1 wherein addresses representing coincidence circuits producing said data signal are applied directly to said address modification storage and an integrator having an initial value of one is connected to said data circuit, and means operable in response to an event signalled by an ECG for changing said region base addresses for addressing said buffer storage, whereby said data correction circuit may be used in an ECG gated ECT.

4. A data correction circuit as claimed in claim 1 and further comprising means for loading a constant into said means for storing as constant, said means for loading a constant comprising means for reading from a memory in the form of a nomograph.

5. A data correction circuit as claimed in claim 1 wherein said arithmetic means includes means for multiplying the uncorrected data by a constant having the value $$Ke^{-\frac{K_1 t}{T}}$$

where K and $K_1$ are constants, T is the half life of a redioistope which produces the positrons, and t is the time which has elapsed since a start of the data correction.

6. A data corwecting circuit as claimed in claim 1 and further comprising sequencing means for sequencing said first and second temporary storages and said constant register whereby said first temporary storage collects uncorrected data while said second temporary storage transfers data to said arithmetic means, and said first temporary storage transfers data to said arithmetic means while said second temporary storage collects uncorrected data, said means for sequencing including means to change the constant in said constant register each time either of said temporary storages transfers uncorrected data to said arithmetic means.

7. A data correction circuit for use in a positron ECT wherein uncorrected data is produced by coincidence circuits upon annihilation of positrons, said data correction circuit comprising:

first and second temporary storages for temporarily storing uncorrected data produced by the coincidence circuits;

a buffer storage for storing corrected data in a plurality of addressable frame regions;

a data circuit and an address circuit connected between said temporary storages and said buffer storage;

an address modification storage connected in said address circuit;

an adder responsive to said address modification storage and a source of frame region base addresses for addressing said buffer storage;

means for storing a constant;

arithmetic means connected in said data circuit for performing dead time and decay correction on said uncorrected data as it is transferred from said first and second temporary storages to said buffer storage, said arithmetic means including means for multiplying uncorrected data received from said temporary storage by a constant from said means for storing a constant;

sequencing means for sequencing said first and second temporary storages and said means for storing a constant whereby said first temporary storage collects uncorrected data while said second temporary storage transfers uncorrected data to said arithmetic means and said first temporary storage transfers data to said arithmetic means while said second temporary storage means collects uncorrected data; and a counter responsive to the coincidence circuits for controlling said sequencing means to load a constant in said means for storing a constant each time one of said temporary storages transfers uncorrected data to said arithmetic means.

* * * * *